(12) United States Patent
Manabe et al.

(10) Patent No.: US 7,480,616 B2
(45) Date of Patent: Jan. 20, 2009

(54) INFORMATION RECOGNITION DEVICE AND INFORMATION RECOGNITION METHOD

(75) Inventors: Hiroyuki Manabe, Yokosuka (JP); Akira Hiraiwa, Yokohama (JP); Toshiaki Sugimura, Yokohama (JP)

(73) Assignee: NTT DoCoMo, Inc., Tokyo (JP)

( * ) Notice: Subject to any disclaimer, the term of this patent is extended or adjusted under 35 U.S.C. 154(b) by 750 days.

(21) Appl. No.: 10/373,730

(22) Filed: Feb. 27, 2003

(65) Prior Publication Data

US 2003/0163306 A1      Aug. 28, 2003

(30) Foreign Application Priority Data

Feb. 28, 2002    (JP)    ............................ P2002-054235

(51) Int. Cl.
  *G10L 15/04*    (2006.01)
(52) U.S. Cl. ........................ 704/254; 704/243; 704/270; 704/271; 704/249
(58) Field of Classification Search ................. 704/243, 704/254, 270, 271, 249
  See application file for complete search history.

(56) References Cited

U.S. PATENT DOCUMENTS

| | | | | |
|---|---|---|---|---|
| 6,006,175 | A * | 12/1999 | Holzrichter | 704/208 |
| 6,629,072 | B1 * | 9/2003 | Thelen et al. | 704/251 |
| 6,795,807 | B1 * | 9/2004 | Baraff | 704/271 |
| 6,941,264 | B2 * | 9/2005 | Konopka et al. | 704/243 |
| 6,970,819 | B1 * | 11/2005 | Tabei | 704/256 |
| 6,999,925 | B2 * | 2/2006 | Fischer et al. | 704/243 |
| 2002/0194005 | A1 * | 12/2002 | Lahr | 704/271 |

FOREIGN PATENT DOCUMENTS

| | | |
|---|---|---|
| CN | 1150852 A | 5/1997 |
| CN | 1298171 A | 6/2001 |
| DE | 42 12 907 | 10/1993 |
| JP | 2-77800 | 3/1990 |
| JP | 6-012483 | 1/1994 |
| JP | 7-181888 | 7/1995 |

OTHER PUBLICATIONS

A. D. C. Chan, et al., 2001 Proceeding of the 23rd Annual EMBS International Conference, pp. 1727-1730, XP-002239576, "Hidden Markov Model Classification of Myoelectric Signals in Speech", Oct. 25-28, 2001.

(Continued)

*Primary Examiner*—Vijay B Chawan
(74) *Attorney, Agent, or Firm*—Oblon, Spivak, McClelland, Maier & Neustadt, P.C.

(57) ABSTRACT

Information relating to an amount of muscle activity is extracted from a myo-electrical signal by activity amount information extraction means, and information recognition is performed by activity amount information recognition means using the information relating to the amount of muscle activity of a speaker. There is a prescribed correspondence relationship between the amount of muscle activity of a speaker and a phoneme uttered by a speaker, so the content of an utterance can be recognized with a high recognition rate by information recognition using information relating to an amount of muscle activity.

9 Claims, 9 Drawing Sheets

OTHER PUBLICATIONS

M. S. Morse, et al., IEEE Engineering in Medicine & Biology Society 11th Annual International Conference, pp. 1793-1794, XP-010088605, "Use of Myoelectric Signals to Recognize Speech", 1989.

M. S. Morse, et al., Annual International Conference of the IEEE Engineering in Medicine and Biology Society, vol. 13, No. 4, pp. 1877-1878, XP-01010949, "Speech Recognition Using Myoelectric Signals With Neural Networks", 1991.

J. F. Holzrichter, et al., Journal of the Acoustical Society of America, vol. 103, No. 1, pp. 622-625, XP-000731768, "Speech Articulator Measurements Using Low Power EM-Wave Sensors", Jan. 1998.

N. Sugie, et al., IEEE Transactions on Biomedical Engineering, vol. BMB-32, No. 7, pp. 485-490, "A Speech Prosthesis Employing a Speech Synthesizer Vowel Discrimination From Perioral Muscle Activities and Vowel Production", Jul. 1985.

Shinji Fujita, et al., "Pattern Classification of Vowels Based on EMG Signals Using Neural Network", 10th Academic Lecture Meeting of the Society of Instrument and Control Engineers, Chugoku Branch, 712, Dec. 1, 2001, pp. 308-309.

* cited by examiner

MAIN TIME WINDOW OR SUBSIDIARY TIME WINDOW $$\text{ROOT MEAN SQUARE} = \sqrt{\frac{1}{2T}\int_{-T}^{T} e^2(t+\tau)d\tau}$$

$$\text{AVERAGE RECTIFIED VALUE} = \int_{-\infty}^{\infty} h(\tau)|e(t+\tau)|d\tau \quad \text{WHERE} \quad \int_{-\infty}^{\infty} h(\tau)d\tau = 1$$

$$\text{INTEGRATED AVERAGE VALUE} = \int_{T}^{T+\Delta T} |e(t+\tau)|d\tau$$

|  |  | PHONEME | | | | | |
| --- | --- | --- | --- | --- | --- | --- | --- |
|  |  | "a" | "i" | "u" | ...... | "wo" | "n" |
| MUSCLE | ORBICULARIS ORIS MUSCLE | 2 | 3 | 5 |  | 5 | 3 |
|  | BUCCINATOR MUSCLE | 2 | 5 | 1 |  | 1 | 1 |
|  | ZYGOMATICUS MAJOR MUSCLE | 1 | 5 | 1 |  | 1 | 1 |
|  | ZYGOMATICUS MINOR MUSCLE | 3 | 4 | 2 |  | 1 | 1 |
|  | RISORIUS MUSCLE | 1 | 5 | 2 |  | 2 | 2 |
|  | . | . | . | . | ...... | . | . |
|  | . | . | . | . | ...... | . | . |
|  | . | . | . | . | ...... | . | . |
|  | . | . | . | . | ...... | . | . |
|  | MENTALIS MUSCLE | 4 | 3 | 1 |  | 1 | 2 |
|  | PLATYSMA MUSCLE | 1 | 3 | 1 |  | 2 | 2 |

INFORMATION RECOGNITION DEVICE AND INFORMATION RECOGNITION METHOD

BACKGROUND OF THE INVENTION

1. Field of the Invention

The present invention relates to an information recognition device and information recognition method wherein the content of an utterance is recognized using the myo-electrical signals of the speaker's muscles when speaking.

2. Related Background Art

Information recognition devices are previously known whereby the content of an utterance is recognized using the myo-electrical signal generated by movement etc of perioral muscles of the person performing the speaking action, independently of sound. In this way, information recognition from the movement of the mouth or tongue etc can be achieved without the speaker generating sound. This is very useful in noisy environments or in places where silence is required.

Methods of information recognition from myo-electrical signals in such an information recognition device include for example: as disclosed in Noboru Sugie et al., "A speech employing a speech synthesizer vowel discrimination from perioral muscles activities and vowel production", IEEE transactions on Biomedical Engineering, vol. 32, No. 7, 1985, pp 485-490, a method of information recognition in which the five vowels (a, i, u, e, o) are discriminated by passing a myo-electrical signal through a bandpass filter and counting the number of crossings of a threshold value; as disclosed in Laid-open Japanese Patent Publication Number H. 7-181888, a method of detection of not just vowels but also consonants from a speaker by using an neural network to process a power spectrum obtained by FFT processing of the myo-electrical signals of perioral muscles; or as disclosed in Laid-open Japanese Patent Publication Number H. 6-12483, a method of converting the amplitude of a myo-electrical signal into binary form using a threshold value and processing this using a neural network.

SUMMARY OF THE INVENTION

However, the information recognition methods described above were subject to the problem that it was not possible to improve the recognition rate of the content of utterances significantly.

In view of the above, an object of the present invention is to provide an information recognition device and information recognition method with a high recognition rate.

An information recognition device according to the present invention that recognizes the content of an utterance using a myo-electrical signal of a muscle of a speaker when the speaker is speaking, comprises: myo-electrical signal acquisition means that acquires said myo-electrical signal; activity amount information extraction means that extracts information relating to the activity amount of said muscle from said myo-electrical signal; and information recognition means that recognizes the content of said utterance using information relating to the amount of activity of said muscle.

An information recognition method according to the present invention wherein the content of an utterance is recognized using a myo-electrical signal of a muscle of the speaker when the speaker speaks, comprises: a myo-electrical signal acquisition step of acquiring said myo-electrical signal; an activity amount information extraction step of extracting information relating to the amount of activity of said muscle from said myo-electrical signal; and an information recognition step in which the content of said utterance is recognized using said information relating to the amount of muscle activity.

With the information recognition device or information recognition method according to the present invention, information relating to muscle activity is extracted from the myo-electrical signal and information recognition is performed using information relating to the amount of muscle activity of the speaker. Since there is a prescribed correspondence relationship between the amounts of muscle activity of the speaker and the phoneme that is being uttered by the speaker, the content of an utterance can be recognized with a high recognition rate by performing information recognition using the information relating to amounts of muscle activity.

Preferably, in said information recognition device, said activity amount information extraction means acquires at least one of the root mean square, average rectified value and integrated average value of said myo-electrical signal as information relating to said amount of muscle activity.

Also preferably, in said information recognition method, in said activity amount information extraction step at least one of the root mean square, average rectified value and integrated average value of said myo-electrical signal is acquired as said information relating to the amount of muscle activity.

Since the root mean square, average rectified value and integrated average value of the myo-electrical signal have a high correlation with the amount of muscle activity, recognition of the content of an utterance can suitably be performed by acquiring the root mean square, average rectified value or integrated average value as information relating to amounts of muscle activity. Also, the computational load for acquiring such averages from the myo-electrical signal is considerably lower than that involved in FFT processing of the myo-electrical signal, as conventionally.

Preferably also, in said information recognition device, said information recognition means recognizes the content of said utterance by means of a neural network that inputs information relating to said amount of muscle activity.

Preferably also, in said information recognition method, in said information recognition step the content of said utterance is recognized by means of a neural network that inputs information relating to said amount of muscle activity.

In this way, the content of an utterance can conveniently be recognized by performing information recognition using a neural network that inputs information relating to amounts of muscle activity.

Said information recognition device may also comprise a database in which phonemes are associated with information relating to amounts of muscle activity of a speaker when the phoneme in question is uttered and said information recognition means may acquire a phoneme uttered by said speaker by referring to said database using information relating to the amount of muscle activity extracted by said activity amount information extraction means.

Also, in said information recognition method, in said information recognition step a phoneme uttered by said speaker may be acquired by referring to a database that associates phonemes with information relating to the amount of muscle activity of the speaker when the phoneme in question is uttered, using information relating to the amount of muscle activity extracted by said activity amount information extraction step.

In this way, the phonemes uttered by a speaker are easily acquired and the content of an utterance conveniently recognized by referring to a database that associates phonemes with information relating to the amount of muscle activity when the phoneme is uttered, using information relating to the amount of muscle activity.

Preferably also, said information recognition device comprises: audio information acquisition means that acquires information relating to sound generated on said utterance; audio information recognition means that recognizes the content of said utterance using information relating to said sound; and learning means that performs learning relating to information recognition by said information recognition means using information relating to amount of muscle activity extracted by said activity amount information extraction means and the content of the utterance constituting the teaching data recognized by said audio information recognition means, and said information recognition means recognizes the content of said utterance by referring to the result of said learning, using information relating to the amount of muscle activity extracted by said activity amount information extraction means.

Preferably also, said information recognition method comprises: an audio information acquisition step of acquiring information relating to sound generated in said utterance; an audio information recognition step of recognizing the content of said utterance using information relating to said sound; and a learning step of performing learning relating to information recognition in said information recognition step using information relating to the amount to muscle activity extracted by said activity amount information extraction step and the content of an utterance constituting teaching data recognized by said audio information recognition step, and in said information recognition step, the content of said utterance is recognized by referring to the results of said learning, using information relating to the amount of muscle activity extracted by said activity amount information extraction step.

By means of such learning, information recognition adapted to the speaker can be achieved and the recognition rate even further increased. Also, since teaching data is generated by information recognition using sound during an utterance, learning can be performed using free utterances without the speaker being conscious of it and the load on the speaker during learning is thereby reduced.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

A preferred embodiment of an information recognition device according to the present invention is described in detail below with reference to the appended drawings.

Figure 1:
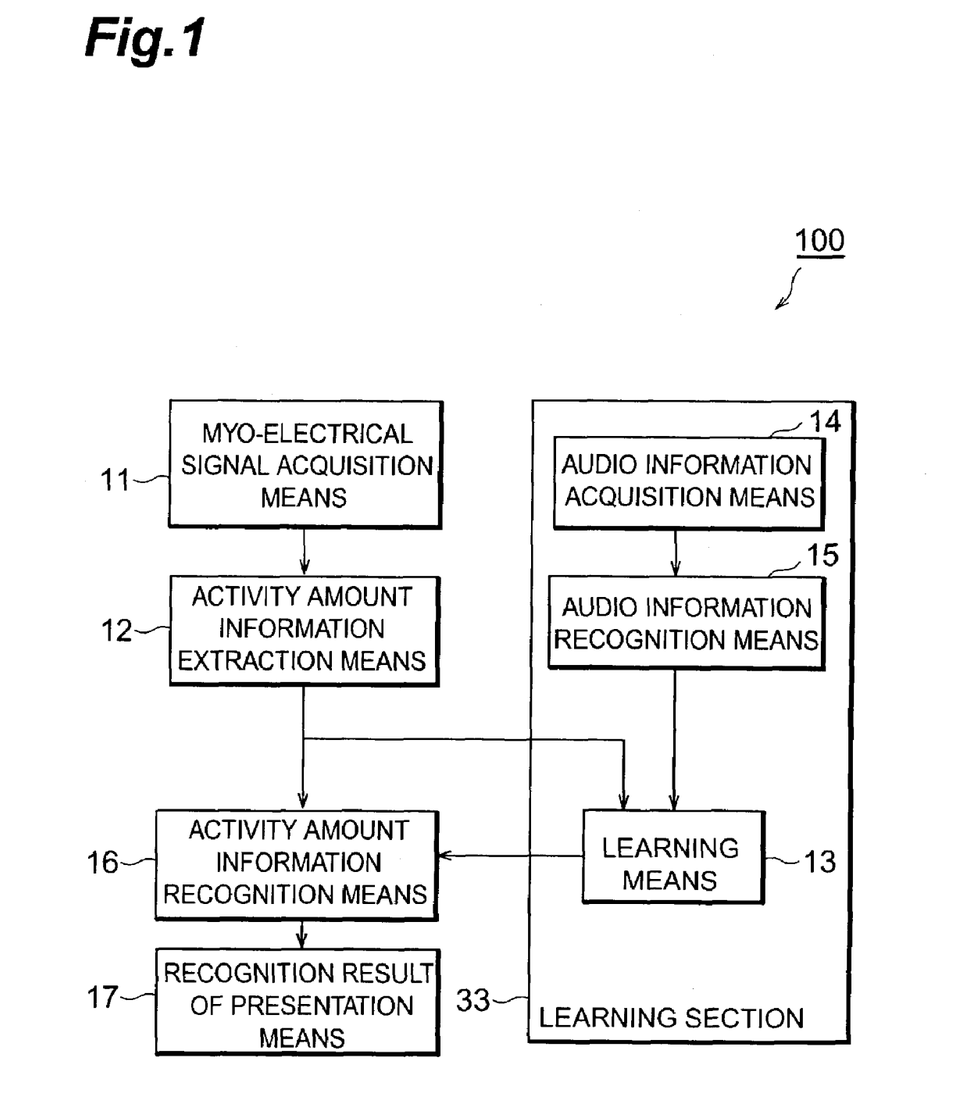
FIG. 1 is a block diagram showing an information recognition device according to a first embodiment.

FIG. 1 is a block diagram of an information recognition device according to a first embodiment. The information recognition device 100 according to this embodiment is an information recognition device that recognizes the content of an utterance of a speaker who performs an unvoiced speaking action i.e. a speaking action without generating voice and comprises: myo-electrical signal acquisition means 11 that acquires a myo-electrical signal from a speaker; activity amount information extraction means 12 that extracts information relating to the amount of muscle activity from a myo-electrical signal; activity amount information recognition means (corresponding to information recognition means) 16 that performs information recognition of utterance content of a speaker using information relating to the amount of muscle activity; recognition results presentation means 17 that presents the results of information recognition; and a learning section 33 that performs learning relating to information recognition in the activity amount information recognition means 16.

Figure 2A:
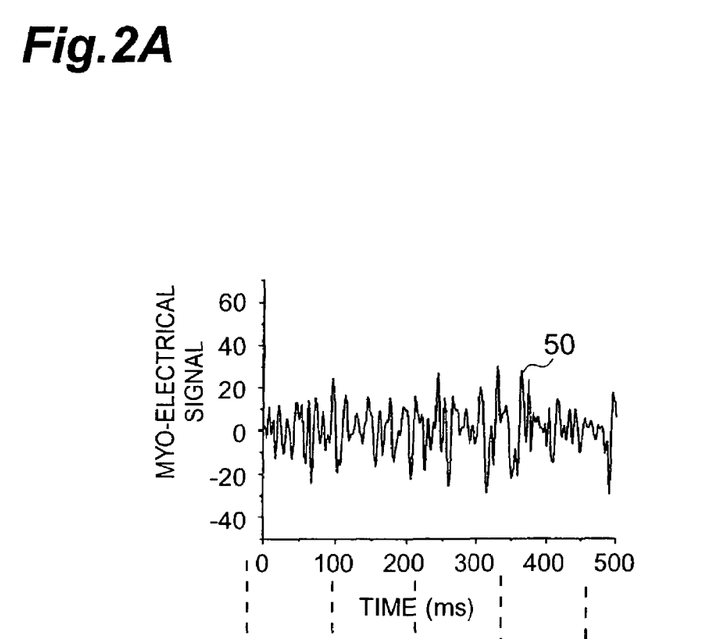
FIGS. 2A and 2B are views given in explanation of a method of windowing a myo-electrical signal by a time window in the activity amount information extraction means in FIG. 1.

The myo-electrical signal acquisition means 11 acquires fluctuations etc of myo-electrical signals produced by activity of perioral muscles (articulatory organs) when the speaker performs a speech action and amplifies the acquired myo-electrical signals. In order to perform information recognition with high accuracy, it is desirable to acquire myo-electrical signals of a plurality of perioral muscles. An example of a myo-electrical signal acquired in this way is shown in FIG. 2A. The horizontal axis is the time and the vertical axis is the potential of the myo-electrical signal.

Returning to FIG. 1, the activity amount information extraction means 12 windows the myo-electrical signal amplified by the myo-electrical signal acquisition means 11 in prescribed time windows and extracts information relating to the amount of muscle activity from the myo-electrical signal in each of these time windows.

Figure 2B:
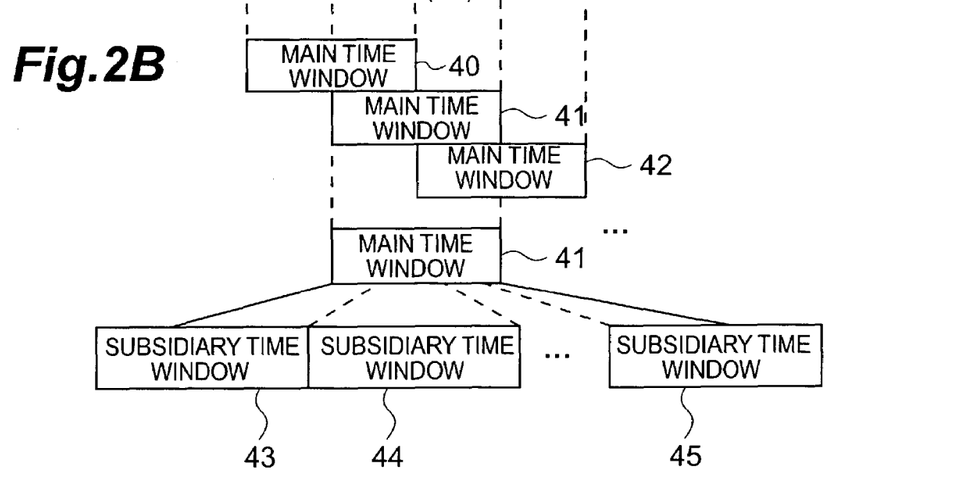

Specifically, first of all, as shown in FIG. 2A and FIG. 2B, the myo-electrical signal 50 acquired by the myo-electrical signal acquisition means 11 is sequentially windowed by main time windows 40, 41, 42 etc of prescribed length. These main time windows 40, 41, 42 are assumed to be of the same time length and the starting times of these main time windows 40, 41, 42 are successively delayed by a prescribed time in each case, for example by half of the time length of the main time windows in each case. Also, if required, the respective main time windows 41 etc can be further divided into any desired number of subsidiary time windows 43, 44, 45. Recognition of vowels may be chiefly performed using the main time windows 40, 41, 42 etc and recognition of consonants may be performed using the subsidiary time windows 43, 44, 45 etc.

Figure 3A:
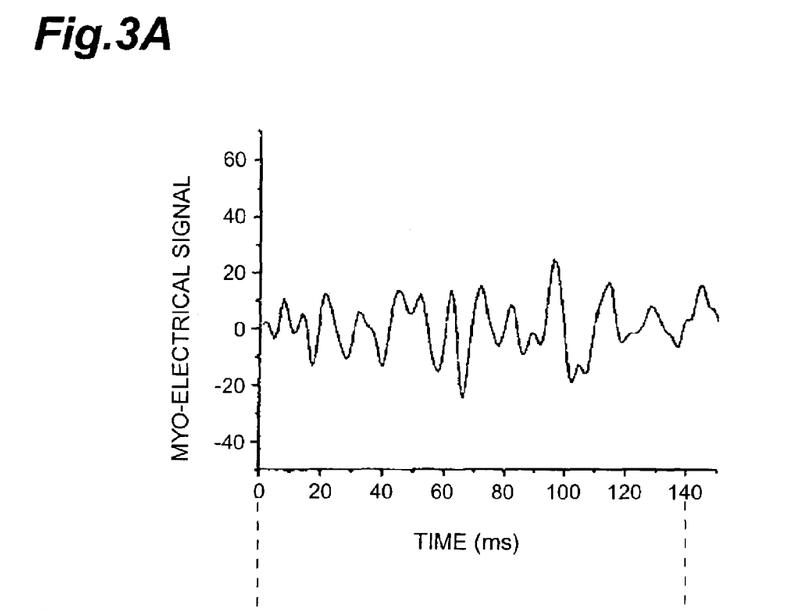
FIG. 3A and FIG. 3B are views given in explanation of a method of acquiring information relating to the amount of muscle activity from the extracted myo-electrical signal, in the activity amount information extraction means in FIG. 1.
Figure 3B:
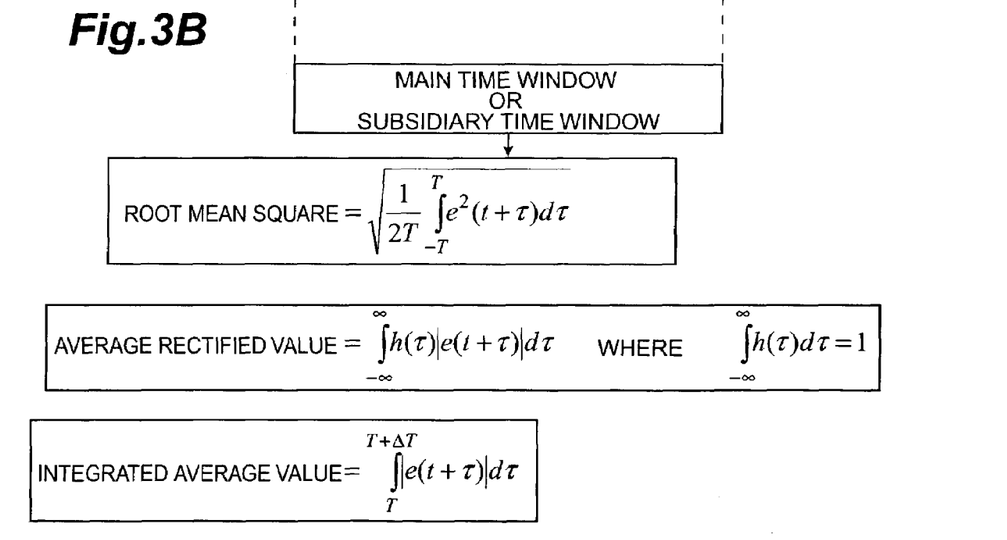

Next, as information relating to the amount of muscle activity in respect of the respective main time window 41 etc or the subsidiary time window 43 etc, as shown in FIG. 3A and FIG. 3B, the root mean square (RMS) of the myo-electrical signal is calculated. The root mean square is defined by the following expression, where e(t) is the potential of the myo-electrical signal (EMG).

$$RMS = \sqrt{\frac{1}{2T}\int_{-T}^{T} e^2(t-\tau)d\tau} \quad (1)$$

Other quantities that may be employed that are correlated with the amount of muscle activity are the average rectified value (ARV) of the myo-electrical signal, expressed by formula (2) or the integrated average value of the myo-electrical signal (IEMG), expressed by expression (3), etc all these may be employed in combination.

$$ARV = \int_{-\infty}^{+\infty} h(\tau)|e(t+\tau)|d\tau \quad (2)$$

$$\text{where } \int_{-\infty}^{+\infty} h(\tau)d\tau = 0$$

$$IEMG = \int_{T}^{T+\Delta T} |e(t+\tau)|d\tau \quad (3)$$

The reasons for extracting information regarding the amount of muscle activity in this way from the myo-electrical signal will now be described.

Figure 4:
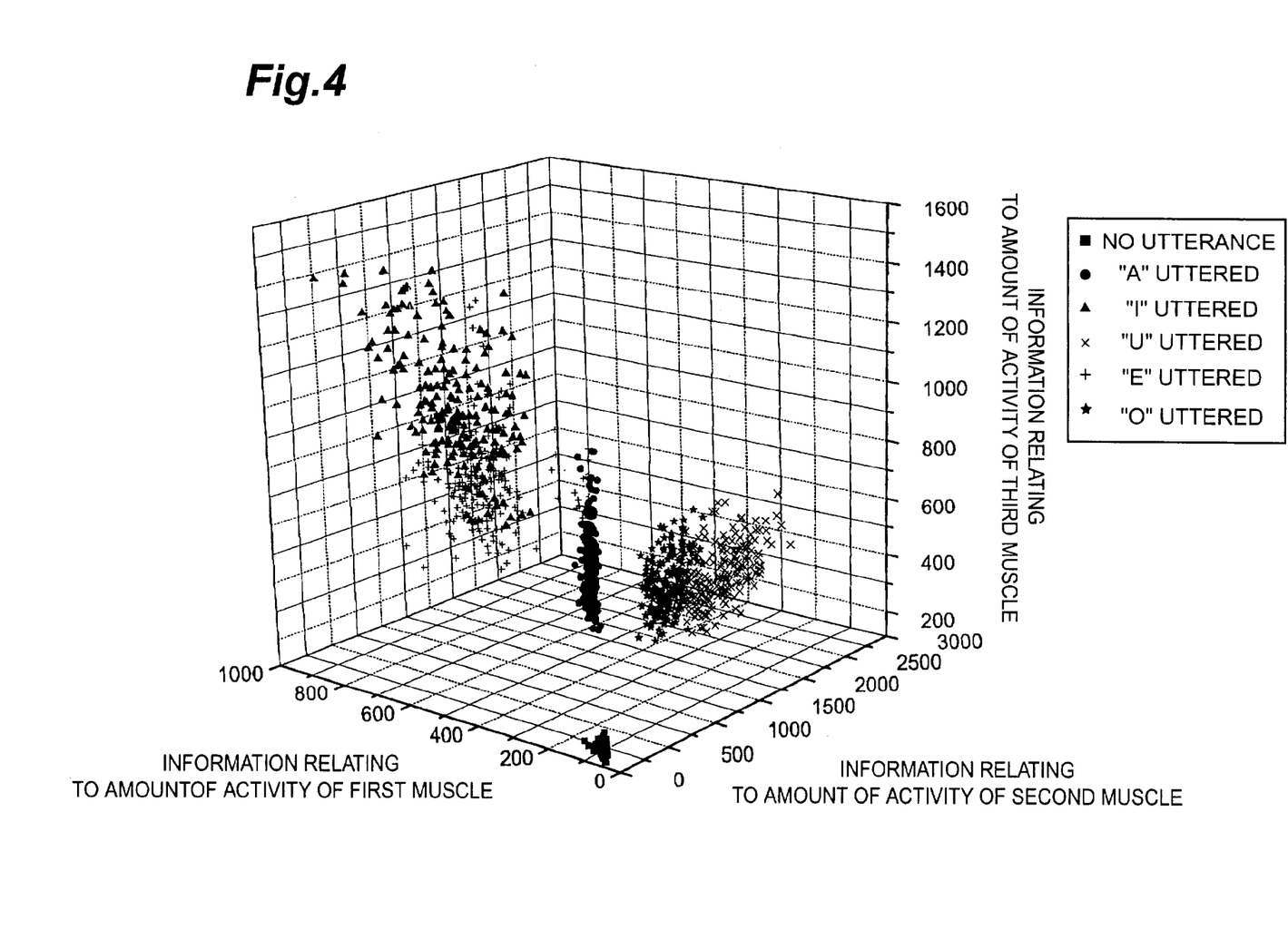
FIG. 4 is a view showing information relating to the amount of muscle activity of three perioral muscles when not speaking and when uttering "a", "i", "u", "e", and "o"

The amounts of activity of the respective perioral muscles of a speaker when a speaker pronounces phonemes such as vowels or consonants are different for each phoneme. FIG. 4 shows the results of plotting on the X axis, Y axis and Z axis respectively the root mean squares of the respective acquired myo-electrical signals representing the amounts of activity of three representative perioral muscles of a speaker when the speaker is pronouncing respectively "a", "i", "u", "e", and "o" and when in the relaxed condition i.e. not speaking.

As can be seen from FIG. 4, the magnitudes of the amounts of activity of the respective muscles when not speaking and when pronouncing "a", "i", "u", "e", and "o" are mutually different and it can be seen that there is a prescribed correspondence relationship between the amounts of activity of the respective muscles and the respective phonemes. Information recognition with a high recognition rate can therefore easily be achieved by extracting information relating to the amounts of activity of the muscles from the myo-electrical signals and acquiring the phonemes corresponding to the information relating to the amounts of activity of these muscles.

Next, returning to FIG. 1, the activity amount information recognition means 16 recognizes the content of the speaker's utterance by acquiring the phonemes pronounced by the speaker, by using the information relating to the amounts of muscle activity acquired in this way.

Figure 5:
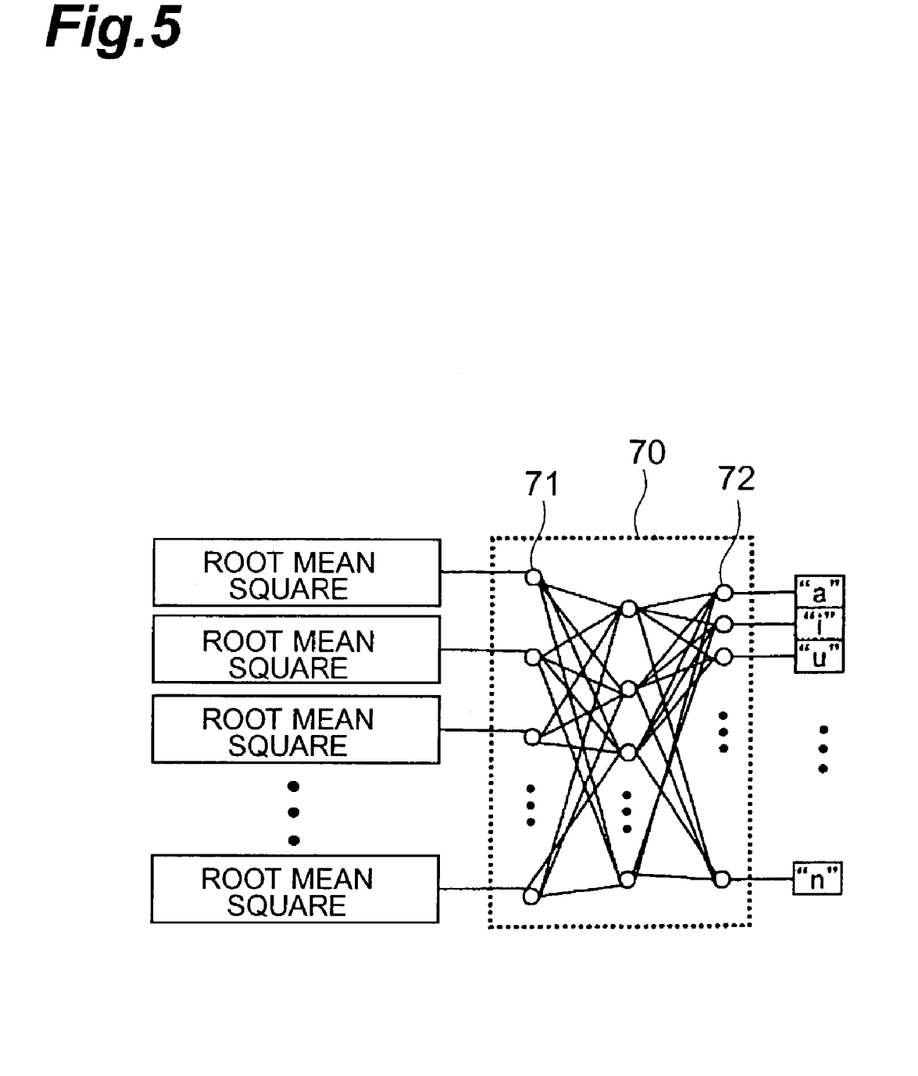
FIG. 5 is a view showing a neural network in activity amount information recognition means in FIG. 1.

Specifically, as shown in FIG. 5, information recognition is performed by a neural network 70 of three-layer structure. Specifically, to the input layer 71 there is input information, such as for example the root mean square, relating to the amount of activity of the respective muscles acquired by the activity amount information extraction means 12. The output layer 72 is constituted as a unit responsive to phonemes, for example vowels and consonants such as "a", "i", "u", " . . . ", and "n". This neural network 70 identifies phonemes in the utterance in question using prescribed recognition parameters, from the information relating to amounts of muscle activity that is input to the input layer 71, and outputs these to the output layer 72; the content of the utterance is thereby recognized.

For the recognition parameters in this neural network 70, universal recognition parameters that have been prepared beforehand or recognition parameters etc adapted to the speaker, generated by a learning section 33, to be described, may be employed.

Returning to FIG. 1, the recognition results presentation means 17 presents the recognition results recognized by the activity amount information recognition means 16 to the speaker by means of a display or speaker etc, or transfers them to an application such as a word processor, or transmits them to another party etc by communication means etc.

The learning section 33 comprises audio information acquisition means 14, audio information recognition means 15 and learning means 13. The audio information acquisition means 14 acquires an audio signal generated when the speaker generates voice i.e. when the speaker performs a voiced speaking action and acquires audio information by performing spectral analysis and/or cepstrum analysis etc of the acquired audio signal.

The audio information recognition means 15 acquires the content of the speaker's utterance by performing voice recognition using the audio information acquired by the audio information acquisition means 14 and uses this to provide teaching data corresponding to the content of the speaker's utterance. There are no particular restrictions regarding the voice recognition method in the audio information recognition means 15 and for example a hidden Markov model using spectral envelopes etc or DP matching method etc may be employed.

The learning means 13 acquires information relating to the amount of muscle activity extracted by the activity amount information extraction means 12 and, as teaching data, acquires the content of the utterance acquired by the audio information recognition means 15, carries out learning relating to the information recognition performed by the activity amount recognition means 16 and thereby generates recognition parameters for this information recognition.

Specifically, if, as in this embodiment, a neural network 70 is employed (see FIG. 5) by the activity amount information recognition means 16, adopting the back propagation method for this neural network 70, the root mean square etc of the myo-electrical signal constituting the information relating to the amount of muscle activity is supplied to the input layer 71 while the respective content of the utterances recognized by the audio information recognition means 15 of the output layer 72 may be supplied thereto as the phonemes "a", "i", "u", " . . . ", and "n"; in this way, recognition parameters adapted to each speaker may be generated.

Next, the operation of such an information recognition device 100 is described and an information recognition method according to this embodiment is also described concurrently.

Figure 6:
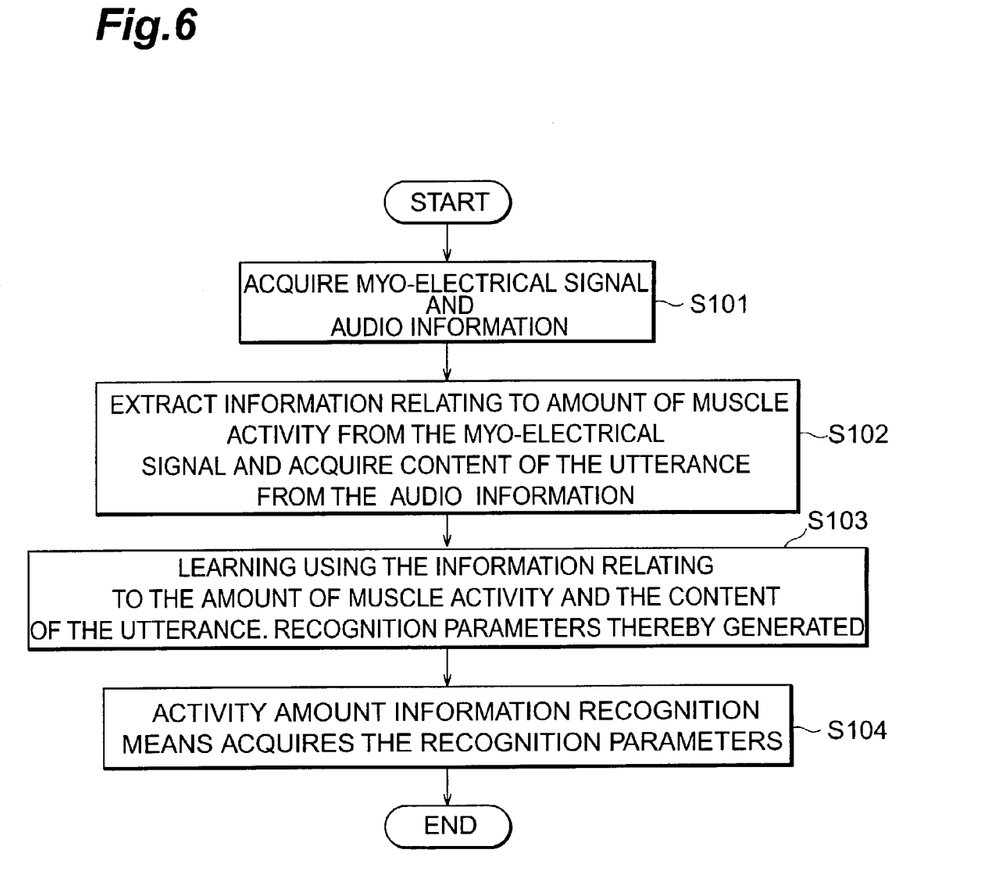
FIG. 6 is a flow chart showing a procedure whereby learning relating to information recognition is performed in a first embodiment.

First of all, a procedure for learning relating to information recognition will be described with reference to FIG. 6.

First of all, the information recognition device 100 acquires myo-electrical signals of the speaker's muscles when the speaker is freely generating voiced speech and acquires audio information based on the sound generated with this speech (step 101).

Next, the myo-electrical signals are windowed in prescribed time windows and information relating to the amount of muscle activity in each time window is extracted, while the content of the utterance is extracted (step 102) by performing voice recognition on the audio information.

Next, recognition parameters for information recognition are generated (step 103) by performing learning relating to information recognition by the activity amount information recognition means 16 based on the information relating to the amounts of muscle activity and the content of an utterance constituting teaching data.

The activity amount of information recognition means 16 then acquires the recognition parameters (step 104).

Figure 7:
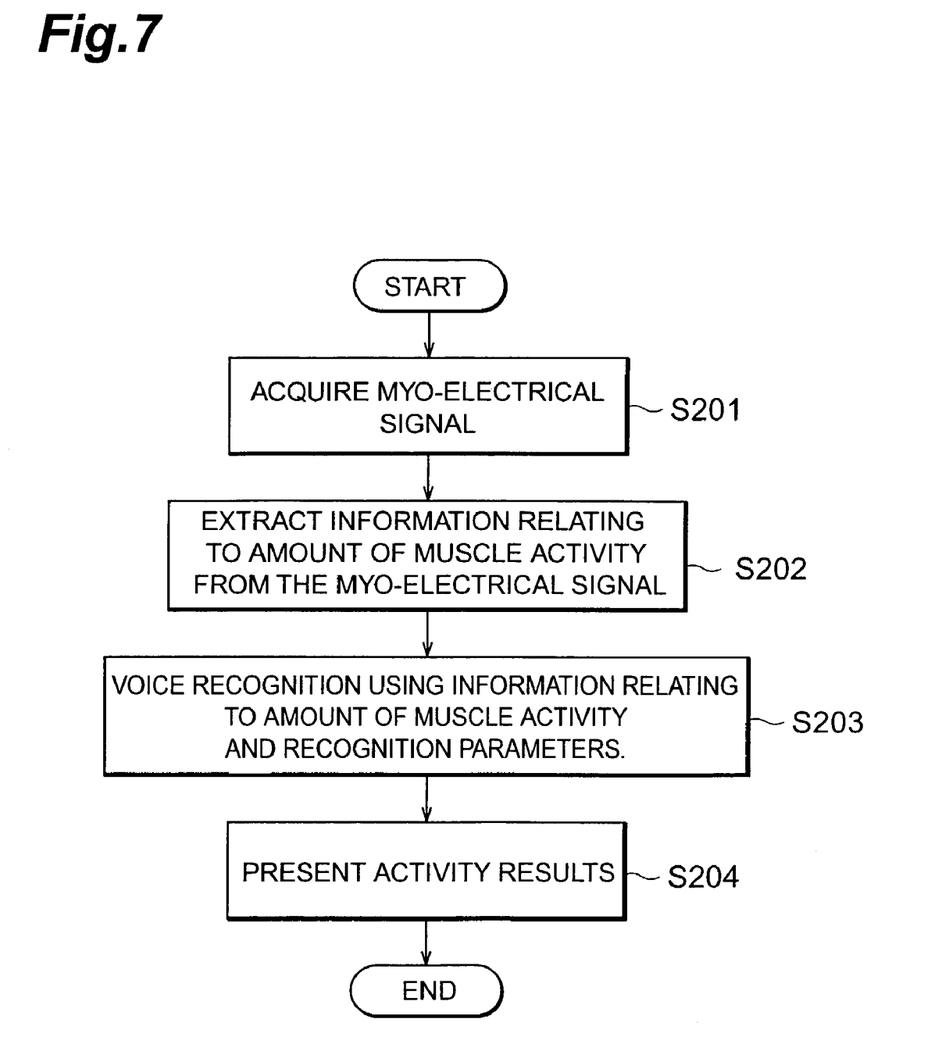
FIG. 7 is a flow chart showing a procedure whereby information recognition is performed using unvoiced utterances in the first embodiment.

Next, referring to FIG. 7, the procedure for performing information recognition using unvoiced utterances of the speaker will be described.

First of all, the information recognition device 100 acquires myo-electrical signals from the speaker when the speaker is generating an unvoiced utterance (step 201).

Next, the myo-electrical signal is windowed in prescribed time windows and information relating to the amount of muscle activity in each time window is extracted (step 202).

Next, the content of the utterance is recognized (step 203) by performing information recognition by means of the neural network 70, using the recognition parameters etc acquired by the learning described above, and using the information relating to amounts of muscle activity.

The recognition results are then output to a screen or by voice or transmitted to an application such as a word processor (step 204).

In this way, with the information recognition device and information recognition method according to this embodiment, information relating to amounts of muscle activity is extracted from the myo-electrical signals and information recognition is performed using the information relating to the amounts of muscle activity of the speaker. Since there is a prescribed correspondence relationship between the amounts of the speaker's muscle activity and the phonemes uttered by the speaker, recognition of the content of an utterance can be achieved with a high recognition rate by information recognition using the information relating to amounts of muscle activity.

Also, since the root mean square, average rectified value and integrated average value of the myo-electrical signal have a high correlation with the amount of muscle activity, recognition of the content of an utterance can suitably be performed by acquiring this root mean square, average rectified value and integrated average value as information relating to amount of muscle activity. Also, the computational load for acquiring these averages from the myo-electrical signals is considerably lower than that of conventional processing of the myo-electrical signal using FFT processing.

Also, the content of utterances can be suitably recognized by performing information recognition using a neural network that inputs information relating to amounts of muscle activity.

In addition, information recognition adapted to a speaker can be achieved by learning enabling an even higher recognition rate to be achieved. Also, since, in this learning, the teaching data is generated by voice-recognition using the sounds during utterance, learning is performed using free speech without the speaker being conscious of it, so the load on the speaker during learning is reduced.

It should be noted that information recognition could be achieved in the same way even without performing learning as described above, by setting universal recognition parameters in respect of the activity amount information recognition means 16 beforehand. Preferably, also, in order to achieve information recognition with a high recognition factor, information regarding amounts of muscle activity is obtained for a large number of muscles.

Figure 8:
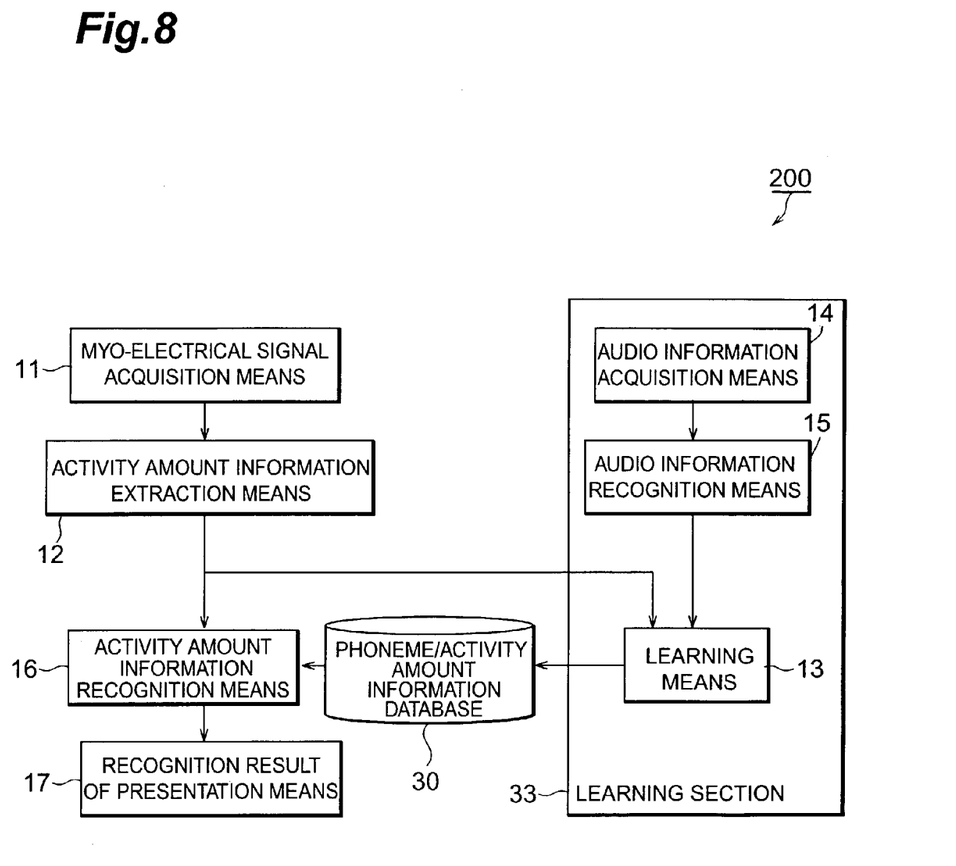
FIG. 8 is a block diagram showing an information recognition device according to a second embodiment.

Next, an information recognition device 200 according to a second embodiment is described with reference to FIG. 8. The difference of the information recognition device 200 of this embodiment and the information recognition device 100 of the first embodiment lies in the provision of a phoneme/activity amount information database (database) 30. The phoneme/activity amount information databas 30 stores phenomes and the information relating to the amounts of muscle activity when these phonemes are uttered which are associated with the phenomes in question. Thus, the activity amount information recognition means 16 recognizes the content, of an utterance by referring to the phoneme/activity amount information database 30 based on the information relating to the amounts of muscle activity extracted by the activity amount information extraction means 12, rather than by using a neural network 70.

In this phoneme/activity amount information database 30, there is stored beforehand typical universal data constituting data associating phonemes with information relating to muscle activity when the phoneme in question is uttered, but, if need be, data based on the results of learning by the learning means 13 can be matched with a speaker.

In one example of such a phoneme/activity amount information database 30, for example in accordance with FIG. 4 etc, for each phoneme, the probability distribution of the magnitude of information relating to the amounts of activity of respective muscles when each phoneme is uttered is found and the probability distribution of the magnitude of information relating to the amounts of activity of these muscles is stored in association with each phoneme in the database. If such a database is employed, the activity amount information recognition means 16 can recognize the content of an utterance by acquiring a phoneme having the probability distribution that is closest to the distribution in question by referring to the database, using the distribution of magnitudes of amount of muscle activation extracted by the activation amount information extraction means 12.

Figure 9:
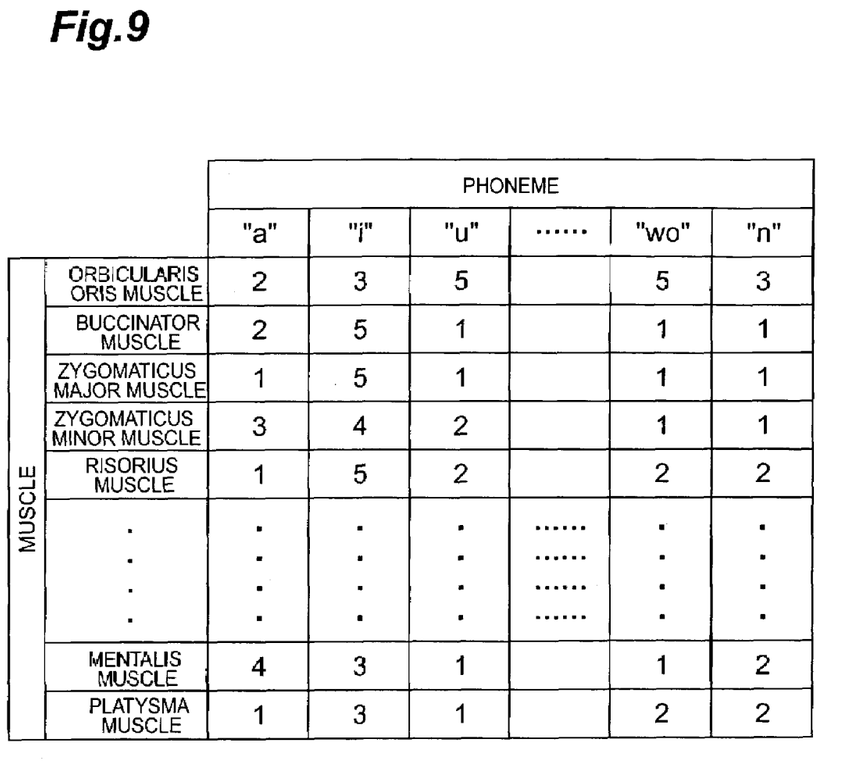
FIG. 9 is a table showing an example of a phoneme activity amount information database of FIG. 8.

Also, as another example of a phoneme/activity amount information database 30, there may be considered for example a table in which respective phonemes are associated with magnitudes of the muscle activity amounts when the phonemes are uttered, as shown in FIG. 9. This table shows the results of evaluating in terms of five levels the degree of activation of each of the perioral muscles when each phoneme is uttered by a typical Japanese person. Even when such a database is employed, the activity amount information recognition means 16 can recognize the content of an utterance by acquiring the phonemes whose muscle activity amount pattern is closest, by referring to the table, using the magnitudes of the muscle activity amounts extracted by the activity amount information extraction means 12.

In this way, in this embodiment, the phonemes uttered by a speaker can easily be acquired and the content of an utterance suitably recognized using acquired information relating to muscle activity, by referring to a database in which the phonemes and information relating to the amounts of muscle activity when the phoneme in question is pronounced are associated.

It should be noted that if such a phoneme/activity amount information database 30 is constructed beforehand, information recognition with a certain level of recognition rate can be achieved even without necessarily performing learning relating to information recognition for each speaker. Also, by performing learning as in the first embodiment, information recognition with a higher recognition rate can be achieved by further adapting this phoneme/activity amount information database 30 to each speaker. It should be noted that, in order to perform information recognition with a high recognition rate, it is desirable to obtain information relating to amounts of muscle activity for a large number of muscles.

It should be noted that an information recognition device according to the present invention is not restricted to the above embodiments and could take various modified forms.

For example, although, in the above embodiments, the learning section 33 acquired utterance content as teaching data by using audio information of the speaker, there is no restriction to this and it would for example be possible for the speaker to directly input the content of an utterance by providing input means such as a keyboard.

It should be noted that, although the information recognition devices 100, 200 of the above embodiments were adapted to information recognition of unvoiced utterances, they could of course perform voiced recognition i.e. information recognition of voiced utterances.

As described above, with the information recognition device and information recognition method according to the present invention, information recognition using information relating to amounts of muscle activity of a speaker is performed by extracting information relating to amounts of muscle activity from a myo-electrical signal. Thus, since there is a prescribed correspondence relationship between the amounts of muscle activity of a speaker and the phonemes uttered by the speaker, recognition of the content of utterances can be achieved with a high recognition rate by performing information recognition using information relating to amounts of muscle activity.

From the invention thus described, it will be obvious that the invention may be varied in many ways. Such variations are not to be regarded as a departure from the spirit and scope of the invention, and all such modifications as would be obvious to one skilled in the art are intended for inclusion within the scope of the following claims.

The basic Japanese Applications No. 2002-54235 filed on Feb. 28, 2002 is hereby incorporated by reference.

What is claimed is:

1. An information recognition device that recognizes content of an utterance of a speaker using a myo-electrical signal of a muscle of the speaker when the speaker is speaking, comprising:
   a myo-electrical signal acquisition unit configured to acquire said myo-electrical signal;
   an activity amount information extraction unit configured to extract information of an activity amount of said muscle from said myo-electrical signal;
   an information recognition unit configured to recognize the content of said utterance using said information of the activity amount of said muscle;
   an audio information acquisition unit configured to acquire audio information of sound generated on said utterance, said audio information being different from said information of an activity amount of said muscle;
   an audio information recognition unit configured to recognize the content of said utterance using said audio information; and
   a learning unit configured to perform learning of recognizing the content of said utterance using said information of the activity amount of said muscle and produce recognition parameters, by using said information of the activity amount of said muscle extracted by said activity amount information extraction unit and the content of the utterance recognized by said audio information recognition unit as teaching data,
   wherein said information recognition unit is configured to recognize content of a respective utterance of the speaker by referring to the result of the learning unit, using a neural network that receives respective information of an activity amount of said muscle extracted by said activity amount information extraction unit as an input and provides the input to an output layer that recognizes contents of the respective utterance using the recognition parameters produced by the learning unit.

2. The information recognition device according to claim 1, wherein said activity amount information extraction unit is configured to acquire at least one of the root mean square, average rectified value and integrated average value of said myo-electrical signal as said information of said activity amount of said muscle.

3. The information recognition device according to claim 1, wherein the activity amount information extraction unit is configured to place the myo-electrical signal into respective time windows and extract the information of an activity amount of the muscle from the myo-electrical signal in the respective time windows.

4. The information recognition device according to claim 3, wherein each of the respective time windows are further divided into subsidiary time windows, and the information recognition unit is configured to perform recognition of vowels using the respective time windows and recognition of consonants using the subsidiary time windows.

5. An information recognition device that recognizes content of an utterance of a speaker using a myo-electrical signal of a muscle of the speaker when the speaker is speaking, comprising:
   a myo-electrical signal acquisition unit configured to acquire said myo-electrical signal;
   an activity amount information extraction unit configured to extract information of an activity amount of said muscle from said myo-electrical signal;
   an information recognition unit configured to recognize the content of said utterance using said information of the activity amount of said muscle;
   an audio information acquisition unit configured to acquire audio information of sound generated on said utterance, said audio information being different from said information of an activity amount of said muscle;
   an audio information recognition unit configured to recognize the content of said utterance using said audio information;
   a learning unit configured to perform learning of recognizing the content of said utterance using said information of the activity amount of said muscle, by using said information of the activity amount of said muscle extracted by said activity amount information extraction unit and the content of the utterance recognized by said audio information recognition unit as teaching data; and
   a database in which phonemes are associated with information of amounts of muscle activity of a speaker when the phoneme is uttered,
   wherein said information recognition unit is configured to recognize content of a respective utterance of the speaker by referring to the result of the learning unit, using respective information of an activity amount of said muscle extracted by said activity amount information extraction unit, and determine a phoneme uttered by said speaker by referring to said database and acquiring a phoneme that has a probability distribution closest to a probability distribution of a magnitude of said information of the activity amount of said muscle extracted by said activity amount information extraction unit.

6. The information recognition device according to claim 5, wherein the activity amount information extraction unit is configured to place the myo-electrical signal into respective time windows and extract the information of an activity amount of the muscle from the myo-electrical signal in the respective time windows.

7. The information recognition device according to claim 6, wherein each of the respective time windows are further divided into subsidiary time windows, and the information recognition unit is configured to perform recognition of vowels using the respective time windows and recognition of consonants using the subsidiary time windows.

8. An information recognition method for recognizing content of an utterance of a speaker, using a myo-electrical signal of a muscle of the speaker when the speaker speaks, comprising:
   acquiring said myo-electrical signal;
   extracting information of an activity amount of said muscle from said myo-electrical signal;
   recognizing the content of said utterance, using said information of the activity amount of said muscle;
   acquiring audio information of sound generated on said utterance, said audio information being different from said information of an activity amount of said muscle;
   recognizing the content of said utterance using said audio information;
   learning of recognizing the content of said utterance using said information of the activity amount of said muscle and producing recognition parameters by using said information of the activity amount of said muscle extracted and the content of the utterance recognized using said audio information as teaching data; and
   recognizing content of a respective utterance of the speaker by referring to the result of the learning, using a neural network that receives respective information of an activity amount of said muscle extracted as an input and provides the input to an output layer that recognizes the content of said respective utterance using the recognition parameters produced in said learning.

9. An information recognition method for recognizing content of an utterance of a speaker, using a myo-electrical signal of a muscle of the speaker when the speaker speaks, comprising:
   acquiring said myo-electrical signal;
   extracting information of an activity amount of said muscle from said myo-electrical signal;
   recognizing the content of said utterance, using said information of the activity amount of said muscle;
   acquiring audio information of sound generated on said utterance, said audio information being different from said information of an activity amount of said muscle;
   recognizing the content of said utterance using said audio information;
   learning of recognizing the content of said utterance using said information of the activity amount of said muscle, by using said information of the activity amount of said muscle extracted and the content of the utterance recognized using said audio information as teaching data;
   recognizing content of a respective utterance of the speaker by referring to the result of the learning, using respective information of an activity amount of said muscle extracted; and
   determining a phoneme uttered by said speaker by referring to a database in which phonemes are associated with information of amounts of muscle activity of a speaker when the phoneme is uttered, and acquiring a phoneme that has a probability distribution closest to a probability distribution of a magnitude of said information of the activity amount of said muscle extracted.

* * * * *